United States Patent [19]
Asgharnejad et al.

[11] Patent Number: 6,129,932
[45] Date of Patent: Oct. 10, 2000

[54] COMPOSITIONS FOR INHIBITING PLATELET AGGREGATION

[75] Inventors: Mandana Asgharnejad, Lansdale, Pa.; Prafull K. Shiromani, Neshanic Station, N.J.

[73] Assignee: Merck & Co., Inc., Rahway, N.J.

[21] Appl. No.: 09/145,871

[22] Filed: Sep. 3, 1998

Related U.S. Application Data

[60] Provisional application No. 60/058,085, Sep. 5, 1997.
[51] Int. Cl.$^7$ ................ A61K 9/16; A61K 9/20
[52] U.S. Cl. ............................ 424/489; 424/465
[58] Field of Search ...................... 424/489, 465

[56] References Cited

U.S. PATENT DOCUMENTS

| | | | |
|---|---|---|---|
| 4,609,675 | 9/1986 | Franz | 514/568 |
| 4,840,799 | 6/1989 | Appelgren et al. | 424/493 |
| 4,950,484 | 8/1990 | Olthoff et al. | 424/464 |
| 5,049,394 | 9/1991 | Howard et al. | 424/490 |
| 5,069,910 | 12/1991 | Kovacic et al. | 424/464 |
| 5,281,585 | 1/1994 | Duggan et al. . | |
| 5,455,243 | 10/1995 | Duggan, II . | |
| 5,605,889 | 2/1997 | Curatolo et al. | 514/29 |
| 5,660,860 | 8/1997 | Fielden | 424/464 |
| 5,684,018 | 11/1997 | Alexander, I | 514/316 |
| 5,738,872 | 4/1998 | Ortyl et al. | 424/452 |
| 5,837,292 | 11/1998 | Dijkgraaf et al. | 424/494 |

FOREIGN PATENT DOCUMENTS

9735615A1  10/1997  WIPO .

OTHER PUBLICATIONS

Hutchinson et al J. Med. Chem 39(23):4583–4591, p 7, 8, 1996.
Cook et al J. Pharmacol. Exp. Ther 278(1):62–73, p 10, 1996.
Alexander et al II J. Med. Chem 39(2):480–486, p 12, 1996.
Duggan et al (IV) Book of Abstracts 210$^{th}$ ACS Meeting Chicago IL PT2–062 MED, p 15, Aug. 20, 1995.
Duggan et al (I–II–III) J. Med. Chem. 38(17):3332–3341, p 16, 1995.

*Primary Examiner*—Shep K. Rose
*Attorney, Agent, or Firm*—Richard S. Parr; Melvin Winokur

[57] ABSTRACT

The invention is a pharmaceutical composition for oral administration to a patient comprising pharmaceutically effective amount of [3(R)-[2-Piperidin-4-yl)ethyl]-2-piperidone-1]acetyl-3(R)-methyl-β-alanine, or a pharmaceutically acceptable salt thereof; pharmaceutically acceptable amounts of a polymeric binder; and pharmaceutically acceptable amounts of pharmaceutically acceptable excipients.

The invention is also a process for making a pharmaceutical composition comprising [3(R)-[2-Piperidin-4-yl)ethyl]-2-piperidone-1]acetyl-3(R)-methyl-β-alanine, which comprises the steps of a) mixing, in a vessel suitable for granulation, a pharmaceutically acceptable amount of [3(R)-[2-Piperidin-4-yl)ethyl]-2-piperidone-1]acetyl-3(R)-methyl-β-alanine with pharmaceutically acceptable amounts of a pharmaceutically acceptable binder and with pharmaceutically acceptable amounts of pharmaceutically acceptable disintegrants and with pharmaceutically acceptable amounts of pharmaceutically fillers or diluents;

b) adding a granulating fluid to the mixture during mixing of step a) to form granules;

c) drying the granules to form dried granules;

d) milling the dried granules to form milled granules;

e) lubricating the milled granules to form lubricated granules; and f) compressing the lubricated granules into tablets.

3 Claims, No Drawings

COMPOSITIONS FOR INHIBITING PLATELET AGGREGATION

This application claims the priority of Provisional application No. 60/058,085 filed Sep. 9, 1997.

BACKGROUND OF THE INVENTION

The invention relates to compositions for inhibiting the binding of fibrinogen to blood platelets, and inhibiting the aggregation of blood platelets, by binding a fibrinogen receptor antagonist to the GP IIb/IIIa fibrinogen receptor.

Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothelial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

A multitude of compounds or peptide analogs which inhibit platelet aggregation by inhibiting binding to a blood platelet by fibrinogen are known. U.S. Pat. No. 5,281,585, describes [3(R)-[2-Piperidin-4-yl)ethyl]-2-piperidone-1]acetyl-3(R)-methyl-β-alanine, shown below as

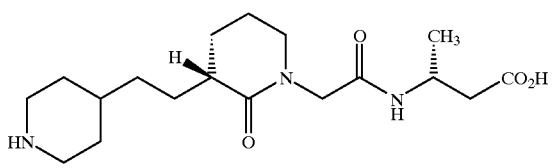

which is useful for preventing and treating diseases caused by thrombus formation. The compound may be administered to patients where prevention of thrombosis by inhibiting binding of fibrinogen to the platelet membrane glycoprotein complex IIb/IIIa receptor is desired. The compound is useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The compound is also useful for long term therapeutic treatment of conditions where inhibition of platelet aggregation is desired.

The compositions of the present invention are safe, storage stable oral compositions which are particularly useful for delivering platelet aggregation inhibitors to patients in need of such inhibition.

SUMMARY OF THE INVENTION

The invention is a pharmaceutical composition comprising a pharmaceutically effective amount of [3(R)-[2-Piperidin-4-yl)ethyl]-2-piperidone-1]acetyl-3(R)-methyl-β-alanine, or a pharmaceutically acceptable salt thereof (also referred to herein as the "active ingredient"); pharmaceutically acceptable amounts of a polymeric binder; and pharmaceutically acceptable amounts of pharmaceutically acceptable excipients.

The composition is a stable and readily disintegratable tablet which is suitable for once or twice a day dosing of the active ingredient.

In one class of compositions of the invention, the amount of [3(R)-[2-Piperidin-4-yl)ethyl]-2-piperidone-1]acetyl-3(R)-methyl-β-alanine is between about 1% and 50% by weight of the composition, and the binder is present in an amount between about 5% and 99% by weight of the composition.

In a subclass of this class, the amount of [3(R)-[2-Piperidin-4-yl)ethyl]-2-piperidone-1]acetyl-3(R)-methyl-β-alanine is between about 1% and 50% by weight of the composition, and the binder is present in an amount between about 5% and 99% by weight of the composition.

In a group of this subclass, the amount of [3(R)-[2-Piperidin-4-yl)ethyl]-2-piperidone-1]acetyl-3(R)-methyl-β-alanine is between about 20% and 30% by weight of the composition, and the binder is present in an amount between about 25% and 50% by weight of the composition.

In a subgroup of this group, the polymeric binder is pregelatinized starch.

The invention is also a process for making a pharmaceutical composition comprising [3(R)-[2-Piperidin-4-yl)ethyl]-2-piperidone-1]acetyl-3(R)-methyl-β-alanine, which comprises the steps of a) mixing, in a vessel suitable for granulation, a pharmaceutically acceptable amount of [3(R)-[2-Piperidin-4-yl)ethyl]-2-piperidone-1]acetyl-3(R)-methyl-β-alanine with pharmaceutically acceptable amounts of a pharmaceutically acceptable binder and with pharmaceutically acceptable amounts of pharmaceutically acceptable disintegrants and with pharmaceutically acceptable amounts of pharmaceutically fillers or diluents;

b) adding a granulating fluid to the mixture during mixing of step a) to form granules;

c) drying the granules to form dried granules;

d) milling the dried granules to form milled granules;

e) lubricating the milled granules to form lubricated granules; and f) compressing the lubricated granules into tablets.

The invention also includes a method for inhibiting the aggregation of blood platelets in a mammal, e.g., a human, comprising treating the mammal with a pharmaceutically effective amount of the composition of the invention.

Compositions of the invention are useful in the manufacture of a medicament for inhibiting binding of fibrinogen to the platelet membrane glycoprotein complex IIb/IIIa receptor, preventing platelet thrombosis, thromboembolism and reocclusion during and after thrombolytic therapy or after angioplasty or coronary artery bypass procedures, and preventing myocardial infarction in a mammal.

DETAILED DESCRIPTION OF THE INVENTION

Compositions of the present invention are stable, readily disintegratable pharmaceutical tablets which can be made by a process resulting in essentially no active ingredient material loss. The advantage to these compositions is that alternative compositions made with [3(R)-[2-Piperidin-4yl)

ethyl]-2-piperidone-1]acetyl-3(R)-methyl-β-alanine using alternative processes, e.g., those made by direct compression, are more difficult to make due to the zwitterionic nature of the active ingredient, which causes the active ingredient to adhere to surfaces. Active ingredient adherence to surfaces causes a significant amount of active ingredient material loss. The compositions of the invention are made with essentially no active ingredient material loss.

In the oral tablet, the active ingredient can be combined with an oral, non-toxic, pharmaceutically acceptable excipients such as inert fillers including lactose (e.g. spray dried from Foremost Foods Co., San Francisco, Calif.; extrafine crystalline EFK, DMV, Veghel, The Netherlands), starch, sucrose, glucose, mannitol, microcrystalline cellulose (e.g. Avicel® FMC Corp. Philadelphia, Pa.), sorbitol, calcium phosphate dihydrate (e.g. DiTab, Stauffer Chemical Co., Westport, Conn.), and the like; lubricants including sodium oleate, sodium stearate, magnesium stearate, sodium benzoate, sodium acetate and the like; and disintegrating agents including starch and starch derivatives, cellulose derivatives, alginates, microcrystalline cellulose, croscarmellose sodium, crosslinked polyvinyl pyrrolidone, and the like. Coloring and flavoring agents can also be incorporated into the tablet when desired.

Suitable binders for formulating with the active ingredient [3(R)-[2-Piperidin-4-yl)ethyl]-2-piperidone-1]acetyl-3(R)-methyl-β-alanine are polymeric binders. These include polymeric materials such as pre gelatinized starch (Starch 1500, Colorcom, Inc., West Point, Pa.), non-pre gelatinized starch, gelatin, natural and synthetic gums such as acacia, tragacanth or sodium alginate, hydroxymethylcellulose, hydroxypropylcellulose, polyethylene glycol, polyvinylpyrolidone, waxes and the like.

Granulating fluids useful for forming the granules used to make the tablets include aqueous compositions which are typically used to cause powdered pharmaceutical composition material to agglomerate, e.g. water, aqueous ethanol solutions, citric acid solutions, aqueous hydroxypropylcellulose solutions, aqueous polyvinyl pyrrolidinone solutions, and alkali metal citrate solutions, and any other granulating fluid which is typically used in wet granulation processes to form pharmaceutical granules. The fluids may be sprayed into the mixed powder at a given temperature while powder is mixed in a granulator such as a Fukae-Powtec granulator or other high shear granulator equivalent, e.g. from Baker Perkins, Fielder, etc.

Wet granules are dried in, for example, a suitable piece of equipment such as a forced air tray dryer at a temperature range of between ambient and about 80° C., or a fluidized bed dryer. The granules are kept under these conditions for a period of time necessary to obtain acceptable residual moisture levels. Thus it is understood that other commercially available dryers would also be suitable for the practice of this invention provided that the above identified purpose is accomplished by the equipment.

Using milling equipment the dried granules are sized into suitable granular size. Milling reduces the particle size of the large granules to facilitate more uniform distribution during finished dosage form preparation.

The purpose of milling is to reduce the particle size of the large granules. Thus it is understood that commercially available mills fitted with various size screens and run at different impeller speeds would be suitable for the practice of this invention provided that the above-defined purpose is accomplished by the equipment.

The milled granules and lubricant are then mixed in a suitable piece of equipment such as a twin shell blender for a period of time such as three minutes or until there is distribution of the lubricant throughout all granules. The granular mixture is then ready for final dosage form preparation on a tablet press. Thus it is understood that other commercially available blenders would also be suitable for the practice of this invention provided that the above-identified purpose is accomplished by the equipment.

The term "pharmaceutically acceptable salts" means non-toxic salts of the active ingredients which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

The active ingredient included within the compositions of the present invention is chiral; included within the scope of the present invention compositions are those having racemic mixtures and separated enantiomers of the active ingredient. Furthermore, hydrates as well as anhydrous compositions and polymorphs of the active ingredient may be included in compositions of the present invention.

The term "pharmaceutically effective amount" means that amount of a drug or pharmaceutical agent that will elicit the biological or medical response of a tissue, system or animal that is being sought by a researcher or clinician. The term "anti-coagulant" includes, for example, heparin, and warfarin. The term "thrombolytic agent" includes, for example, agents such as streptokinase and tissue plasminogen activator. The term "platelet anti-aggregation agent" includes, for example, agents such as aspirin and dipyridamole.

Compositions of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compositions of this invention may be administered to these surgical patients to prevent the formation of thrombi and thromboemboli. The composition is also useful for long term therapeutic treatment of conditions where inhibition of platelet aggregation is desired.

Extracorporeal circulation is routinely used for cardiovascular surgery in order to oxygenate blood. Platelets adhere to surfaces of the extracorporeal circuit. Adhesion is dependent on the interaction between GP IIb/IIIa on the platelet membranes and fibrinogen adsorbed to the surface of the circuit. (Gluszko et al., *Amer. J. Physiol.*, 252(H), 615–621 (1987)). Platelets released from artificial surfaces show impaired hemostatic function. Compositions of the invention may be administered to prevent adhesion.

Other applications of these compositions include prevention of platelet thrombosis, thromboembolism and reocclusion during and after thrombolytic therapy and prevention of platelet thrombosis, thromboembolism and reocclusion after angioplasty or coronary artery bypass procedures. They may also be used to prevent myocardial infarction.

The compositions can also be co-administered with the usual doses of suitable anticoagulation agents, such as heparin or warfarin (typically given in tablet doses between 1 and 20 mg daily during administration of the active drug), or thrombolytic agents such as tissue plasminogen activator (typically given in i.v. doses of between 20 and 150 mg over two hour period prior to or during administration of the active drug), to achieve beneficial effects in the treatment of various vascular pathologies. Such co-administration also includes administration if the active drug with doses of anticoagulant agents or thrombolytic agents less than the usual doses of those agents.

The dosage regimen utilizing the compositions of the present invention is selected in accordance with a variety of factors including type, species, age, weight, sex and medical condition of the patient; the severity of the condition to be treated; the route of administration; the renal and hepatic function of the patient; and the particular active ingredient or salt thereof employed. An ordinarily skilled physician or veterinarian can readily determine and prescribe the effective amount of the drug required to prevent, counter, or arrest the progress of the condition.

Oral dosages of the present invention, when used for the indicated effects, will range between about 0.04 mg per kg of body weight per day (mg/kg/day) to about 7 mg/kg/day and preferably 0.04–3.3 mg/kg/day and most preferably 0.55–3.3 mg/kg/day. For example, a typical 90 kg patient would receive oral dosages ranging between about 4 mg/day and about 600 mg/day, most preferably between about 50 mg/day and 300 mg/day. Suitable pharmaceutical oral compositions may contain, for example, 2 mg, 10 mg, 25 mg, 50 mg, 100 mg, 120 mg, 150 mg, and 300 mg, administered once or twice a day.

EXAMPLE 1

Compositions containing 2, 25 or 150 mg of [3(R)-[2-Piperidin4-yl)ethyl]-2-piperidone-1]acetyl-3(R)-methyl-β-alanine Tablets containing 2, 25 or 150 mg respectively, of the compound [3(R)-[2-Piperidin-4-yl)ethyl]-2-piperidone-1]acetyl-3(R)-methyl-β-alanine are prepared as illustrated below.

| Ingredients | Amount (mg) | | |
|---|---|---|---|
| [3(R)-[2-Piperidin-4-yl)ethyl]-2-piperidone-1]acetyl-3(R)-methyl-β-alanine | 2.0 | 25.0 | 150 |
| Starch pre gelatinized NF 1500 | 45.6 | 34.05 | 204.3 |
| Avicel PH 101 (Microcrystalline cellulose) | 45.6 | 34.05 | 204.3 |
| Croscarmellose sodium NF | 6.0 | 6.0 | 36.0 |
| Talc | 0.6 | 0.6 | 3.6 |
| Magnesium stearate | 0.3 | 0.3 | 1.8 |
| Absolute ethanol | 7.5 μl | 7.5 μl | 45 μl |
| Water (purified) | 22.5 μl | 22.5 μl | 135 μl |

[3(R)-[2-Piperidin-4-yl)ethyl]-2-piperidone-1]acetyl-3 (R)-methyl-β-alanine, starch, microcrystalline cellulose, one-half quantity of croscarmellose, microcrystalline cellulose, starch pregelatinized, magnesium stearate are placed in a clean Fukae-Powtec granulator or other high shear granulator equivalent e.g., from Baker Perkins, Fielder, etc., and mixed for three minutes. Ethanol and water are mixed in a beaker and then added over a period of 1.5 minutes while the powder mixture is being mixed. The resulting mixture is then granulated for 7 minutes and thereafter collected. The granules are dried at 47° C. in a tray dryer for 3 hours. The dry granules are then milled and mixed with the remaining one-half of croscarmellose. Magnesium stearate and talc are mixed and then added to granule-croscarmellose mixture in a V blender and admixed for 5 minutes. The blended material is then pressed into tablets using an F Press tablet machine or other tablet press.

Tablet hardness evaluation, using standard tablet hardness evaluation procedure, showed that the formed tablet having 2 mg of active ingredient had a hardness of 8.8 kp, and that the formed tablet having 10 mg active ingredient had a hardness of 9 kp.

EXAMPLE 2

Compositions containing 2, 25 or 150 mg of [3(R)-[2-Piperidin4-yl)ethyl]-2-piperidone-1]acetyl-3(R)-methyl-β-alanine The same compositions described in Example 1 are made according to the same procedure except tray drying is replaced with fluidized bed drying.

EXAMPLE 3

Composition containing 50 mg [3(R)-[2-Piperidin-4-yl)ethyl]-2-piperidone-1]acetyl-3(R)-methyl-β-alanine A tablet containing 50 mg [3(R)-[2-Piperidin-4-yl)ethyl]-2-piperidone-1]acetyl-3(R)-methyl-β-alanine and the following additional ingredients was prepared following the procedure described in Example 1.

| Ingredient | Amount (mg) |
|---|---|
| [3(R)-[2-Piperidin-4-yl)ethyl]-2-piperidone-1]acetyl-3(R)-methyl-β-alanine | 50.0 |
| Starch pre gelatinized NF 1500 | 68.1 |
| Avicel PH 101 (Microcrystalline cellulose) | 68.1 |
| Croscarmellose sodium NF | 12.0 |
| Talc | 1.2 |
| Magnesium stearate | 0.6 |
| Absolute ethanol | 15.0 μl |
| Water (purified) | 45.0 μl |

Croscarmellose was added in two steps as described in Example 1 except that amount, of 6 mg each rather than 3 mg each were added.

The formulation was studied for stability and shown to be stable, as measure by drug content after 26 weeks of storage at 30° C./75 RH and 40° 0C./75 RH and 30° C. ambient conditions (RH is relative humidity). Tablet hardness evaluation, using standard tablet hardness evaluation procedure, showed that the formed tablet had a hardness of 8 kp.

A material balance study of the tablets prepared in Example 2 shows that essentially 100% of the amount of [3(R)-[2-Piperidin4-yl)ethyl]-2-piperidone-1]acetyl-3(R)-methyl-β-alanine added to the granulator was usefully incorporated into the finished product (i.e., no loss of [3(R)-[2-Piperidin-4-yl)ethyl]-2-piperidone-1]acetyl-3(R)-methyl-β-alanine).

What is claimed is:

1. A process for making a pharmaceutical composition comprising [3(R)-[2-Piperidin-4-yl)ethyl]-2-piperidone-1]acetyl-3(R)-methyl-βalanine, which comprises the steps of
   a) mixing, in a vessel suitable for granulation, an amount of about 25% by weight of the composition of [3(R)-[2-Piperidin-4-yl)ethyl]-2-piperidone-1]acetyl-3(R)-methyl-β-alanine with an amount of between about 30% and 35% by weight of the Composition of pregelatinized starch and with pharmaceutically acceptable amounts of pharmaceutically acceptable disintegrants and with pharmaceutically acceptable amounts of pharmaceutically fillers or diluents;
   b) adding a granulating fluid to the mixture during mixing of step a) to form granules;
   c) drying the granules to form dried granules;
   d) milling the dried granules to form milled granules;
   e) lubricating the milled granules to form lubricated granules; and
   f) compressing the lubricated granules into tablets.

2. A product made by the process of claim 1.

3. A method for inhibiting the aggregation of blood platelets in a mammal, comprising orally treating the mammal with a pharmaceutically effective amount of the product of claim 2.

* * * * *